United States Patent
Nishihara et al.

(10) Patent No.: US 9,295,445 B2
(45) Date of Patent: Mar. 29, 2016

(54) ULTRASONIC DIAGNOSIS APPARATUS WITH AUTOMATIC AND MANUAL GAIN SETTING

(75) Inventors: Kuramitsu Nishihara, Otawara (JP); Kenichi Ichioka, Nasushiobara (JP); Atsushi Sumi, Otawara (JP); Muneki Kataguchi, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 490 days.

(21) Appl. No.: 12/861,297

(22) Filed: Aug. 23, 2010

(65) Prior Publication Data
US 2011/0054320 A1    Mar. 3, 2011

(30) Foreign Application Priority Data
Aug. 26, 2009    (JP) ................. 2009-195570

(51) Int. Cl.
*A61B 8/00*    (2006.01)
*G01S 7/52*    (2006.01)

(52) U.S. Cl.
CPC ... *A61B 8/00* (2013.01); *A61B 8/54* (2013.01); *A61B 8/585* (2013.01); *G01S 7/52033* (2013.01)

(58) Field of Classification Search
CPC ........................................................ A61B 8/00
USPC .................... 73/629, 631; 600/437, 442, 443
See application file for complete search history.

(56) References Cited

U.S. PATENT DOCUMENTS

| | | | | |
|---|---|---|---|---|
| 4,432,236 | A | * | 2/1984 | Nagasaki ........................ 73/631 |
| 5,014,711 | A | * | 5/1991 | Nagasaki ...................... 600/443 |
| 6,398,733 | B1 | | 6/2002 | Simopoulos et al. |
| 6,579,238 | B1 | | 6/2003 | Simopoulos et al. |
| 2006/0079776 | A1 | * | 4/2006 | Karasawa ...................... 600/443 |
| 2006/0241456 | A1 | * | 10/2006 | Karasawa ...................... 600/447 |
| 2009/0062648 | A1 | * | 3/2009 | Derby, Jr. ...................... 600/443 |
| 2009/0112096 | A1 | * | 4/2009 | Tamura ........................ 600/454 |

FOREIGN PATENT DOCUMENTS

JP         2004-500915         1/2004

OTHER PUBLICATIONS

Chinese Office Action Issued Jun. 21, 2012 in Patent Application No. 201010265750.3.

* cited by examiner

*Primary Examiner* — Amanda Lauritzen Moher
*Assistant Examiner* — Serkan Akar
(74) *Attorney, Agent, or Firm* — Oblon, McClelland, Maier & Neustadt, L.L.P.

(57) ABSTRACT

According to one embodiment, an ultrasonic diagnosis apparatus includes an ultrasonic probe, transmission unit, reception unit, control unit, adjustment unit, automatic setting unit, switching unit, manual setting unit, correction unit, and generating unit. The adjustment unit adjusts transmission/reception conditions for repeated ultrasonic transmission/reception in accordance with an instruction from the user. The automatic setting unit sets the first gain for correcting an echo signal in accordance with the adjusted transmission/reception conditions. The switching unit switches between activating and stopping the operation of the automatic setting unit. The manual setting unit sets the second gain for correcting an echo signal in accordance with an instruction from the user. The correction unit corrects an echo signal with the first or second gain. When the adjustment unit adjusts a transmission/reception condition while the automatic setting unit stops operation, the correction unit corrects an echo signal with the second gain.

3 Claims, 5 Drawing Sheets

Gain set when scanning condition parameter is adjusted via user interface (UI)

| Manual STC adjustment \ UI gated-gain update function | Active | Inactive |
|---|---|---|
| Yes | 1. Gain set by automatic setting unit (automatic STC) | 3. Gain set by manual setting unit (manual STC) |
| No | 2. Gain set by automatic setting unit (automatic STC) | 4. Gain set by manual setting unit (manual STC) |

Gain set when scanning condition parameter is adjusted via user interface (UI)

| Manual STC adjustment \ UI gated-gain update function | Active | Inactive |
|---|---|---|
| Yes | 1. Gain set by automatic setting unit (automatic STC) | 3. Gain set by manual setting unit (manual STC) |
| No | 2. Gain set by automatic setting unit (automatic STC) | 4. Gain set by manual setting unit (manual STC) |

F I G. 2

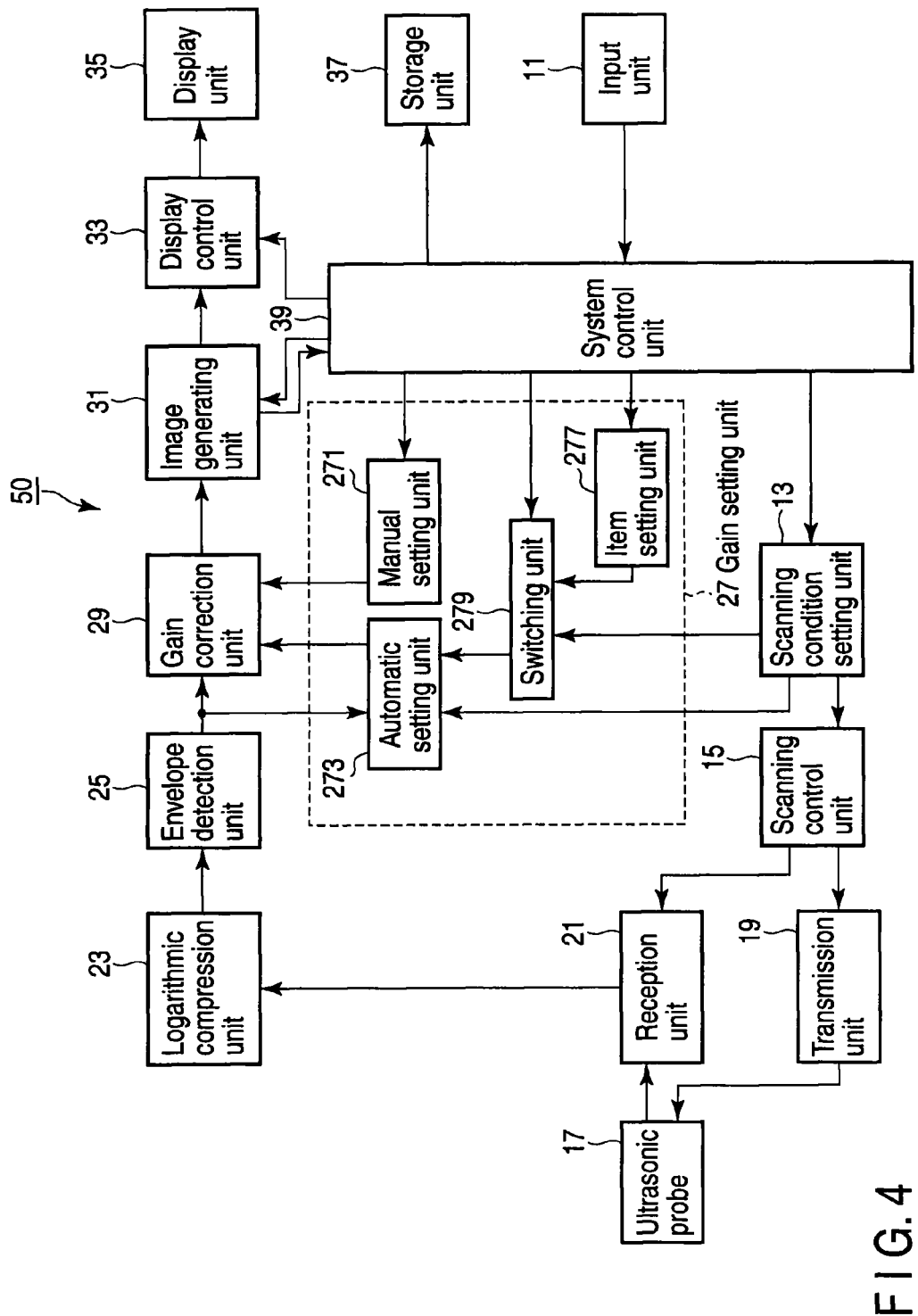
F I G. 4

ULTRASONIC DIAGNOSIS APPARATUS WITH AUTOMATIC AND MANUAL GAIN SETTING

CROSS-REFERENCE TO RELATED APPLICATIONS

This application is based upon and claims the benefit of priority from Japanese Patent Application No. 2009-195570, filed Aug. 26, 2009; the entire contents of which are incorporated herein by reference.

FIELD

Embodiments described herein relate generally to an ultrasonic diagnosis apparatus.

BACKGROUND

An ultrasonic diagnosis apparatus acquires echo signals by ultrasonic scanning and generates display image data based on the acquired echo signals. The ratio of the brightness of each pixel of a display image to the intensity of an echo signal is called a gain. The ultrasonic diagnosis apparatus has a function (STC: Sensitivity Time Control) of adjusting a gain in accordance with the distance in the depth direction so as to display anatomically identical regions on images with the same brightness. As an application of STC, there has been developed a function of automatically adjusting a gain in accordance with the distance in the depth direction by analyzing the intensity of an echo signal. The function of automatically adjusting a gain in accordance with the distance in the depth direction will be referred to as an automatic STC function hereinafter.

In some case, scanning conditions such as a frequency and a focus position are adjusted via a UI (User Interface) during ultrasonic scanning. As a scanning condition is adjusted, the intensity of the echo signal changes. When, therefore, a scanning condition is adjusted, a gain must be set again. For this reason, there has also been developed a function of updating the gain set by the automatic STC function in cooperation with a UI for scanning condition adjustment. The function of updating the gain set by the automatic STC function in cooperation with the UI for scanning condition adjustment will be referred to as a UI gated-gain update function hereinafter. If the gain adjustment accuracy of the automatic STC function is low, STC is manually adjusted in accordance with an instruction from the user via the UI. In general, gain adjustment is repeated by the above automatic STC function, UI gated-gain update function, and manual STC adjustment until a display image with optimal image quality is obtained.

The conventional ultrasonic diagnosis apparatus, however, has the following problem.

In image diagnosis using an ultrasonic diagnosis apparatus, after STC is manually adjusted in accordance with an instruction from the user via the UI, a scanning condition is sometimes changed. In this case, the conventional ultrasonic diagnosis apparatus forcibly resets the manual adjustment result, and automatically executes STC adjustment based on the UI gated-gain update function. If, therefore, the user wants to change only a scanning condition while reflecting the manual adjustment result, he/she needs to manually adjust STC again via the UI after automatic adjustment by the UI gated-gain update function. Therefore, gain adjusting operation sometimes takes much time, resulting in a deterioration in operation efficiency.

BRIEF DESCRIPTION OF THE DRAWINGS

FIG. 2 is a view showing condition-specific gains to be used by a gain correction unit in FIG. 1;

FIG. 4 is a block diagram showing the arrangement of an ultrasonic diagnosis apparatus according to the second embodiment.

DETAILED DESCRIPTION

In general, according to one embodiment, an ultrasonic diagnosis apparatus includes an ultrasonic probe, transmission unit, reception unit, control unit, adjustment unit, automatic setting unit, switching unit, manual setting unit, correction unit, and generating unit. The transmission unit transmits ultrasonic waves to a subject through the ultrasonic probe. The reception unit receives ultrasonic waves reflected by the subject through the ultrasonic probe, and generates echo signals corresponding to the received ultrasonic waves. The control unit controls the transmission unit and the reception unit to repeat ultrasonic transmission/reception through the ultrasonic probe. The adjustment unit adjusts transmission/reception conditions for repeated ultrasonic transmission/reception in accordance with an instruction from the user. The automatic setting unit sets the first gain for correcting an echo signal in accordance with the adjusted transmission/reception conditions. The switching unit switches between activating and stopping the operation of the automatic setting unit. The manual setting unit sets the second gain for correcting an echo signal in accordance with an instruction from the user. The correction unit corrects an echo signal with the first or second gain. When the adjustment unit adjusts a transmission/reception condition while the automatic setting unit stops operation, the correction unit corrects an echo signal with the second gain. The generating unit generates ultrasonic image data based on the corrected echo signal.

An ultrasonic diagnosis apparatus according to an embodiment will be described below with reference to the views of the accompanying drawing.

First Embodiment

Figure 1:
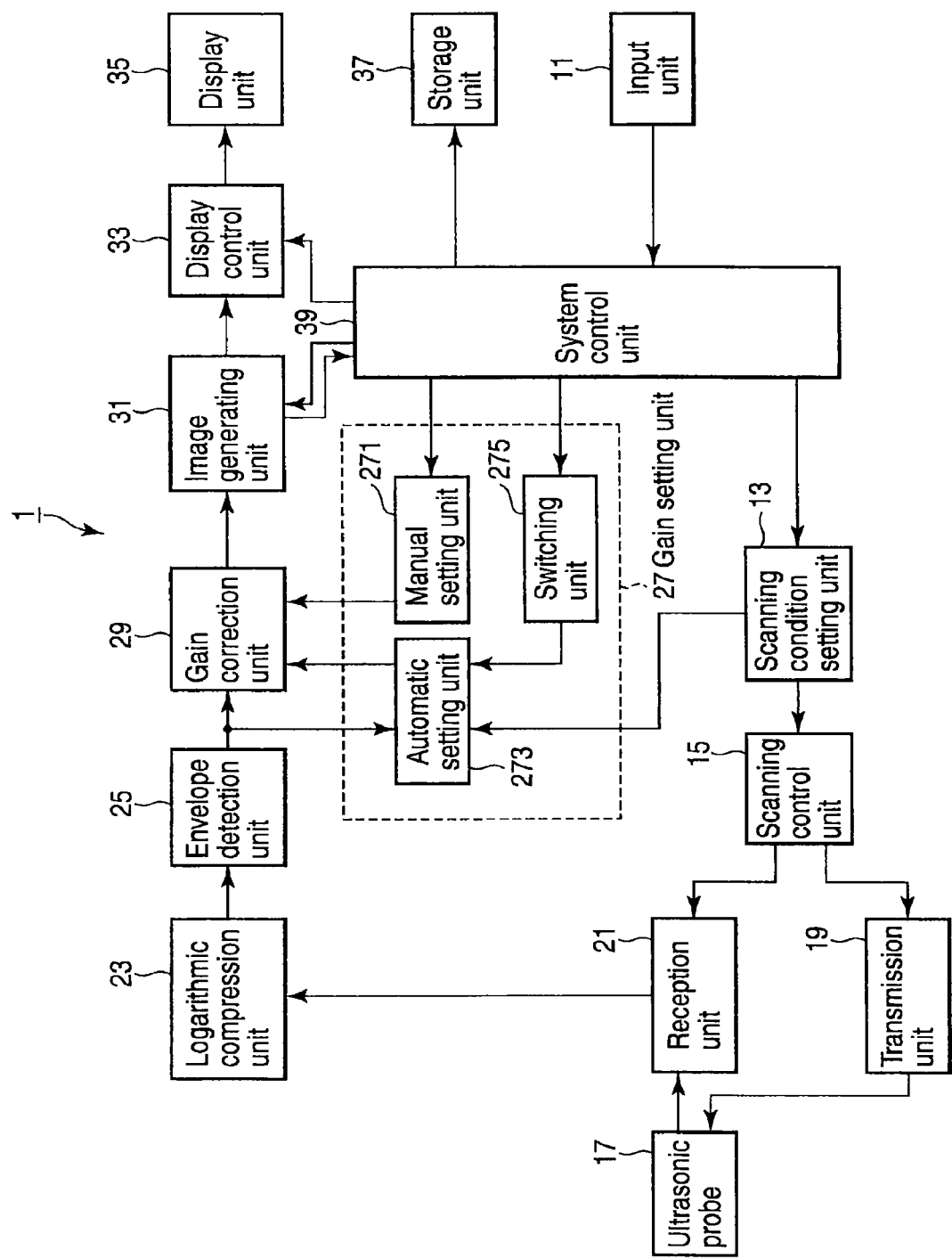
FIG. 1 is a block diagram showing the arrangement of an ultrasonic diagnosis apparatus according to the first embodiment.

FIG. 1 is a block diagram showing the arrangement of an ultrasonic diagnosis apparatus according to the first embodiment. As shown in FIG. 1, an ultrasonic diagnosis apparatus 1 includes an input unit 11, a scanning condition setting unit 13, a scanning control unit 15, an ultrasonic probe 17, a transmission unit 19, a reception unit 21, a logarithmic compression unit 23, an envelope detection unit 25, a gain setting unit 27, a gain correction unit 29, an image generating unit 31, a display control unit 33, a display unit 35, a storage unit 37, and a system control unit 39.

The input unit 11 includes a user interface (to be referred to as a UI hereinafter) such as a brightness adjustment knob (brightness control), in addition to a keyboard and a mouse. The brightness adjustment knob includes a knob for uniformly adjusting the overall brightness of an image, a knob provided for each depth of an image, and a knob provided for each width of an image. The input unit 11 inputs various kinds of instruction and information in accordance with instructions from the user. For example, the input unit 11 detects the position of the knob and outputs the detected position to the system control unit 39. The input unit 11 also includes UIs such as switches for adjusting scanning conditions, a start button for starting scanning, and an end button for ending scanning. The input unit 11 outputs signals corresponding to the switches and buttons to the system control unit 39.

The scanning condition setting unit 13 sets a scanning condition in accordance with an instruction from the user via the input unit 11. If, for example, the user performs scanning condition adjusting operation via the input unit 11 during ultrasonic scanning, the scanning condition setting unit 13 adjusts (re-sets) a scanning condition in accordance with the adjusting operation. In this manner, the scanning condition setting unit 13 also functions as an adjustment unit for scanning conditions. The data of the set scanning condition is supplied to the scanning control unit 15 and an automatic setting unit 273 of the gain setting unit 27.

The scanning control unit 15 controls the transmission unit 19 and the reception unit 21 to repeatedly scan a subject with ultrasonic waves through the ultrasonic probe 17. The scanning control unit 15 controls the transmission unit 19 and the reception unit 21 in accordance with the scanning conditions set by the scanning condition setting unit 13.

Upon receiving a driving pulse from the transmission unit 19, the ultrasonic probe 17 transmits an ultrasonic beam to the subject. The ultrasonic waves transmitted to the subject are sequentially reflected by the discontinuity points (echo sources) of the acoustic impedance in the internal body tissue. The ultrasonic probe 17 receives the reflected ultrasonic waves. The ultrasonic probe 17 converts the received ultrasonic waves into echo signals (electrical signals). The amplitude of each echo signal depends on the difference in acoustic impedance between the body tissue portions on the two sides of an echo source by which an ultrasonic wave is reflected.

The transmission unit 19 repetitively transmits driving pulses to the ultrasonic probe 17 under the control of the scanning control unit 15. With this operation, the transmission unit 19 repetitively transmits ultrasonic beams to the subject through the ultrasonic probe 17. More specifically, the transmission unit 19 repetitively generates rate pulses at a predetermined rate frequency fr Hz (period: 1/fr sec) for each channel. The transmission unit 19 gives each rate pulse a delay time necessary to form a transmission beam in a predetermined beam direction. The transmission unit 19 then generates a driving pulse at the timing based on each delayed rate pulse, and transmits the generated driving pulse to the ultrasonic probe 17. Upon receiving the driving pulse, the ultrasonic probe 17 transmits an ultrasonic beam in the beam direction corresponding to the driving pulse.

The reception unit 21 repetitively receives the ultrasonic waves reflected by the subject as echo signals through the ultrasonic probe 17 under the control of the scanning control unit 15. The reception unit 21 then generates echo signals corresponding to the reception beams based on the received echo signals. More specifically, the reception unit 21 receives echo signals from the ultrasonic probe 17, and amplifies the received echo signals for the respective channels. The reception unit 21 then converts each amplified echo signal from an analog signal to a digital signal. The reception unit 21 stores the digitally converted echo signal in a digital memory. More specifically, each echo signal is stored at an address corresponding to the reception time. The reception unit 21 then calculates a reception time necessary to form a reception beam in a predetermined beam direction for each focus position. The reception unit 21 reads out and adds echo signals from the addresses corresponding to the calculated reception times. Repeating this addition processing will generate an echo signal corresponding to the reception beam in the predetermined beam direction. The generated echo signal is supplied to the logarithmic compression unit 23.

The logarithmic compression unit 23 logarithmically compresses an echo signal from the reception unit 21 to generate a logarithmically compressed echo signal. The intensity of the logarithmically compressed echo signal is proportional to the intensity of the echo signal from the reception unit 21. The logarithmically compressed echo signal is supplied to the envelope detection unit 25.

The envelope detection unit 25 detects the envelope of an echo signal from the logarithmic compression unit 23 to generate an envelope-detected echo signal. The waveform of the envelope-detected echo signal corresponds to the envelope of the waveform of the echo signal from the logarithmic compression unit 23. The envelope-detected echo signal is supplied to the gain correction unit 29 and the automatic setting unit 273 of the gain setting unit 27.

The gain setting unit 27 sets the gain (amplification factor) of an echo signal. There are roughly two types of gain setting methods. One is a method of setting a uniform gain on an ultrasonic image. This method is called 2DGain. The other is a method of setting different gains in accordance with the depths (reception times) from the living body contact surface of the ultrasonic probe 17 to echo sources or beam positions (scanning line positions). The method of setting different gains in accordance with depths is called STC (Sensitive Time Control). The method of setting different gains in accordance with beam positions is called LGC (Lateral Gain Control). A gain is manually set in some cases, and is automatically set in other cases. The gain setting unit 27 can switch between manual setting and automatic setting in response to the execution of a specific user operation as a trigger.

As shown in FIG. 1, the gain setting unit 27 includes a manual setting unit 271, an automatic setting unit 273, and a switching unit 275.

The manual setting unit 271 sets a gain in accordance with an instruction from the user via a knob. More specifically, the manual setting unit 271 sets a gain in accordance with the data of the knob position supplied from the input unit 11. The manual setting unit 271 can be applied to any of 2DGain, STC, and LGC.

The automatic setting unit 273 analyzes the intensity of an echo signal from the envelope detection unit 25 for each reception beam, and automatically sets a gain for each depth. More specifically, the automatic setting unit 273 calculates a gain curve such that the brightness values at anatomically identical regions become uniform on ultrasonic images. A gain curve is a curve indicating the correspondence relationship between echo source depths originating from an echo signal (the reception times of the echo signal) and gains. The gain on the gain curve changes in accordance with a target brightness value. The automatic setting unit 273 automatically sets a gain for each depth in accordance with a calculated gain curve. The function of automatically setting such STC will be referred to as an automatic STC function. The automatic setting unit 273 also has a function of updating a gain by executing the automatic STC function every time a scanning condition is adjusted via the UI of the input unit 11. This function will be referred to as a UI gated-gain update function.

The switching unit 275 switches between activating and stopping the UI gated-gain update function of the automatic setting unit 273 in response to the execution of a specific user operation via the UI of the input unit 11 as a trigger. The specific user operation includes, for example, STC adjusting operation and switching operation of switching between activating and stopping the UI gated-gain update function.

The gain correction unit 29 corrects an echo signal from the envelope detection unit 25 with the gain set by the gain setting unit 27 to generate a gain-corrected echo signal. When a scanning condition is adjusted via the UI of the input unit 11, the gain correction unit 29 corrects the echo signal with the gain set by the manual setting unit 271 in accordance with an instruction from the user or the gain set by the automatic setting unit 273 in accordance with scanning conditions. Note that gain correction is to amplify the intensity of an echo signal with a predetermined gain (amplification factor). More specifically, the gain correction unit 29 corrects an echo signal with the gain set by the automatic setting unit 273 when a scanning condition is adjusted via the UI and the UI gated-gain update function of the automatic setting unit 273 stops.

The image generating unit 31 generates ultrasonic image data based on a gain-corrected echo signal. More specifically, the image generating unit 31 places data in a scan conversion memory in accordance with the position information of a gain-corrected echo signal and interpolates data in data missing portions. This placement processing and interpolation processing will generate ultrasonic image data. Alternatively, the image generating unit 31 may generate volume data based on a gain-corrected echo signal and generate ultrasonic image data associated with a predetermined slice position from the generated volume data. Each pixel constituting an ultrasonic image has a brightness value corresponding to the intensity of the corresponding echo signal. The generated ultrasonic image data is supplied to the display control unit 33. Alternatively, the generated ultrasonic image data is stored in the storage unit 37 via the system control unit 39.

The display control unit 33 displays an ultrasonic image from the image generating unit 31 on the display unit 35. Alternatively, the display control unit 33 displays, on the display unit 35, the ultrasonic image read out from the storage unit 37 by the system control unit 39.

The display unit 35 is a display device such as a CRT display, liquid crystal display, organic EL display, or plasma display.

The storage unit 37 stores the B-mode image data generated by the image generating unit 31. The storage unit 37 also stores a program for performing gain setting processing unique to this embodiment.

The system control unit 39 functions as the nerve center of the ultrasonic diagnosis apparatus 1. The system control unit 39 reads out a program from the storage unit 37 in accordance with an instruction from the user via the input unit 11 and maps the program in the memory. The system control unit 39 then controls the respective units in accordance with the program to execute gain setting processing.

The gains to be used by the gain correction unit 29 will be described next. FIG. 2 shows condition-specific gains to be used by the gain correction unit 29. As shown in FIG. 2, when a scanning condition parameter is adjusted via the UI, the gain correction unit 29 uses different gains depending on whether STC adjustment has been manually performed via the UI and whether the UI gated-gain update function is active or inactive. More specifically, this operation includes the following four patterns. 1 (automatic STC). When STC adjustment has been manually performed and the UI gated-gain update function is active, the gain correction unit 29 performs correction with the gain set by the automatic setting unit 273 using the UI gated-gain update function. 2 (automatic STC). When STC adjustment has not been manually performed and the UI gated-gain update function is active, the gain correction unit 29 performs correction with the gain set by the automatic setting unit 273 using the UI gated-gain update function. 3 (manual STC). When STC adjustment has been manually performed and the UI gated-gain update function is inactive, the gain correction unit 29 performs correction with the gain set by the manual setting unit 271 in accordance with an instruction via the UI. 4. When STC adjustment has not been manually performed and the UI gated-gain update function is inactive, the gain correction unit 29 maintains the current gain.

As indicated by "1" in FIG. 2, when STC adjustment has been manually performed and the UI gated-gain update function is active, the gain correction unit 29 performs correction with the gain set by the automatic setting unit 273 using the UI gated-gain update function. That is, even when gain adjustment is manually performed, if a scanning condition is adjusted afterward, the manually adjusted gain is reset. If the parameter of the adjusted scanning condition greatly contributes to image quality, it is preferable to use the gain automatically set by the UI gated-gain update function, in consideration of the examination efficiency. If, however, the parameter of the adjusted scanning condition does not much contribute to image quality, it is preferable to use the gain manually set immediately before scanning condition adjustment, in consideration of the examination efficiency.

When manual gain setting operation is performed, the switching unit 275 stops the UI gated-gain update function of the automatic setting unit 273. When the user stops the UI gated-gain update function and then performs activating operation for the UI gated-gain update function via the input unit 11, the switching unit 275 reactivates the UI gated-gain update function of the automatic setting unit 273. With this operation, the gain correction unit 29 can selectively correct an echo signal with the gain set by the manual setting unit 271 in accordance with an instruction from the user via the input unit 11 or the gain set by the automatic setting unit 273 using the UI gated-gain update function.

Figure 3:
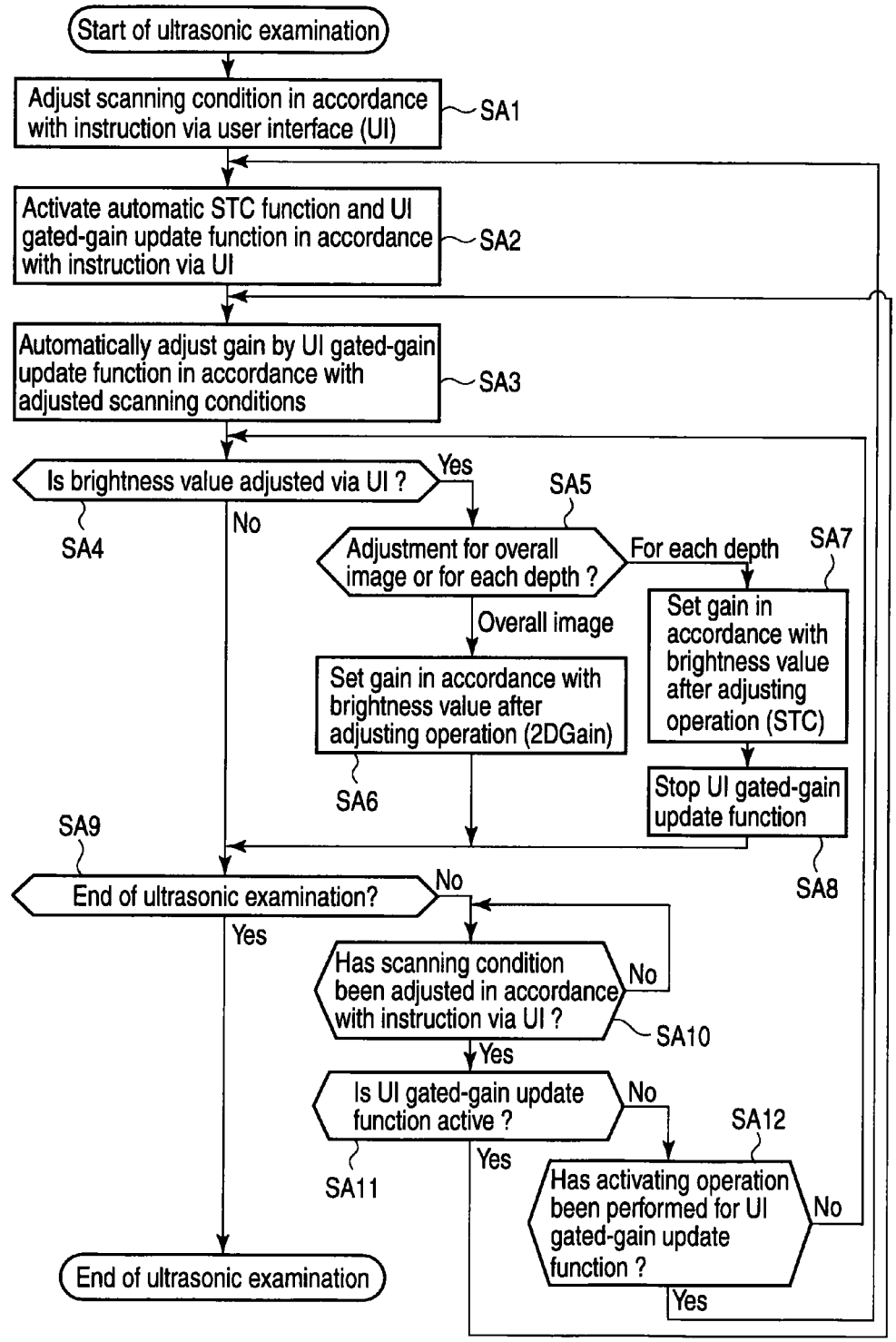
FIG. 3 is a flowchart showing a typical example of a procedure in ultrasonic examination performed under the control of a system control unit in FIG. 1.

A flowchart for ultrasonic examination performed by using the gain setting method unique to the first embodiment will be described next. FIG. 3 is a flowchart showing a typical example of a procedure in ultrasonic examination performed under the control of the system control unit 39 according to the first embodiment. As shown in FIG. 3, when the user issues an instruction to start ultrasonic examination via the input unit 11, the system control unit 39 repeatedly performs ultrasonic scanning by controlling the respective units. The scanning conditions at this stage are those initially set by the scanning condition setting unit 13.

When ultrasonic scanning starts, the display unit 35 displays an ultrasonic image. The user observes this ultrasonic image. Under the initial scanning conditions, optimal ultrasonic examination may not be performed. The user adjusts scanning conditions via the input unit 11 while observing this ultrasonic image. When a scanning condition is adjusted, the intensity of the obtained echo signal changes. As the intensity of the echo signal changes, the brightness value of each pixel of the ultrasonic image also changes. Note that typical scanning condition items include, for example, image quality parameters such as a scanning mode (transmission/reception mode), transmission/reception frequency, focus position, beam density (scanning line density), field angle, slice position, and zoom-in/zoom-out setting (magnification). The scanning mode includes, for example, a fundamental mode using a fundamental ultrasonic wave and a harmonic mode using harmonics. When the user performs scanning condition adjusting operation, the system control unit 39 supplies an input signal corresponding to the adjusting operation to the scanning condition setting unit 13.

Upon receiving the input signal corresponding to the adjusting operation, the scanning condition setting unit 13 adjusts the scanning condition in accordance with the input signal (step SA1). The scanning condition data after the adjustment is supplied to the scanning control unit 15 and the automatic setting unit 273. Upon receiving the scanning condition data after the adjustment, the scanning control unit 15 controls the transmission unit 19 and reception unit 21 in accordance with the scanning conditions and performs ultrasonic scanning in accordance with the scanning conditions after the adjustment.

After adjusting a scanning condition, the user performs activating operation for the automatic STC function and the UI gated-gain update function via the input unit 11. The user performs this activating operation by, for example, pressing the activation button provided for the input unit 11. When the user performs activating operation, the system control unit 39 supplies an input signal corresponding to the activating operation to the switching unit 275.

Upon receiving the input signal corresponding to the activating operation, the switching unit 275 activates the automatic STC function and UI gated-gain update function of the automatic setting unit 273 in accordance with the input signal (step SA2). The automatic setting unit 273 then executes the UI gated-gain update function and updates the gain based on the scanning conditions after the adjustment (step SA3). The updated gain data is supplied to the gain correction unit 29. The gain correction unit 29 corrects the echo signal with the supplied gain. The image generating unit 31 generates ultrasonic image data based on the corrected echo signal. The display control unit 33 displays the generated ultrasonic image on the display unit 35.

The user observes the ultrasonic image corrected by the gain updated by the UI gated-gain update function. In some cases, however, since the gain adjustment accuracy based on the automatic STC function is poor, the brightness of an ultrasonic image based on the UI gated-gain update function does not coincide with the brightness expected by the user. In such a case, the user adjusts the brightness value via the UI to adjust the gain.

When the ultrasonic image is displayed on the display unit 35, the system control unit 39 waits for brightness adjusting operation via the UI (step SA4). Step SA4 continues until the issuance of an instruction to end ultrasonic examination. When the user performs adjusting operation via the UI (YES in step SA4), the system control unit 39 determines whether the brightness adjusting operation is for the entire image or for each depth (step SA5). In other words, the system control unit 39 determines whether the brightness adjusting operation is 2DGain adjusting operation or STC adjusting operation.

2DGain adjusting operation is performed to amplify or attenuate the brightness values of all the pixels of an ultrasonic image with the same value. More specifically, in the case of 2DGain adjusting operation, the user inputs a brightness value for overall brightness (OverAllGain) via a 2DGain knob. When the user inputs a brightness value via the 2DGain knob, the system control unit 39 determines that the brightness adjusting operation is 2DGain adjusting operation (step SA5: for overall image). Upon determining that the brightness adjusting operation is 2DGain adjusting operation, the system control unit 39 sets a gain for the overall image in accordance with the brightness value after the adjusting operation (step SA6). For example, the manual setting unit 271 updates the gain in accordance with the increment (or the decrement) between the brightness value before the adjusting operation and the brightness value after the adjusting operation. The set gain data is supplied to the gain correction unit 29.

STC adjusting operation is performed to amplify or attenuate the brightness values of an ultrasonic image with different values in accordance with the depths, i.e., the reception times of echo signals. More specifically, in the case of STC brightness adjusting operation, the user inputs a brightness value for each depth via an STC knob. When the user inputs brightness values via the STC knob, the system control unit 39 determines that the brightness adjusting operation is STC adjusting operation (step SA5: for each depth). Upon determining that the adjusting operation is STC adjusting operation, the system control unit 39 causes the manual setting unit 271 to set gains for the respective depths in accordance with the brightness values after the adjusting operation (step SA7). For example, the manual setting unit 271 updates the gains for the respective depths, in accordance with the increments (or the decrements) between the brightness values before the adjusting operation and the brightness values after the adjusting operation. The set gain data for each depth is supplied to the gain correction unit 29. Upon executing step SA7, the system control unit 39 causes the switching unit 275 to stop the UI gated-gain update function (step SA8). That is, in step SA8, the switching unit 275 stops the UI gated-gain update function of the automatic setting unit 273. When the UI gated-gain update function stops, even if a scanning condition is adjusted via the UI, the gain is not automatically updated in accordance with the scanning conditions after adjustment.

When 2DGain adjusting operation is performed in step SA6 or STC adjusting operation is performed in step SA8, ultrasonic scanning is repeated with the gain after adjustment. This ultrasonic scanning is performed with the gain expected by the user, and hence can be said to be optimal ultrasonic scanning. When optimal ultrasonic scanning is performed, the user issues an instruction to end ultrasonic examination or performs scanning condition adjusting operation for the next examination.

Upon determining in step SA4 that brightness value adjusting operation has not been performed or performing 2DGain adjusting operation in step SA6 or STC adjusting operation in step SA8, the system control unit 39 determines whether the user has issued an instruction to end ultrasonic examination via the UI (step SA9). Upon determining that the user has not issued an instruction to end ultrasonic examination (NO in step SA9), the system control unit 39 waits until a scanning condition is adjusted in accordance with an instruction via the UI (step SA10). When the user performs scanning condition adjusting operation via the UI and the scanning condition setting unit 13 adjusts a scanning condition in accordance with the adjusting operation (YES in step SA10), the system control unit 39 determines whether the UI gated-gain update function is active (step SA11).

When the processing proceeds in the following sequence: (NO in step SA4)→(NO in step SA9)→(YES in step SA10) or (YES in step SA4)→(step SA5: overall image)→(step SA6)→(NO in step SA9)→(YES in step SA10), the UI gated-gain update function of the automatic setting unit 273 is active at the time of step SA11. That is, when STC adjusting operation has not been performed, the UI gated-gain update function of the automatic setting unit 273 is active at the time of step SA11. Upon determining in step SA11 that the UI gated-gain update function of the automatic setting unit 273 is active (YES in step SA11), the system control unit 39 advances to step SA3. That is, the system control unit 39 repeats ultrasonic scanning under the scanning conditions newly adjusted by the scanning condition setting unit 13 in step SA10 with the gain adjusted by the automatic setting unit 273 based on the scanning conditions.

When the processing proceeds in the following sequence: (YES in step SA4)→(step SA5: for each depth)→(step SA7)→(step SA8)→(NO in step SA9)→(YES in step SA10), the UI gated-gain update function of the automatic setting unit 273 is inactive at the time of step SA11. That is, when STC adjusting operation is performed, the UI gated-gain update function of the automatic setting unit 273 is inactive at the time of step SA11. Upon determining in step SA11 that the UI gated-gain update function is not active (NO in step SA11), the system control unit 39 advances to step SA11.

Upon determining in step SA11 that the UI gated-gain update function is not active (NO in step SA11), the system control unit 39 determines whether the user has performed stating operation for the UI gated-gain update function via the UI (step SA12).

If, for example, the system control unit 39 determines in step SA10 that an image quality parameter that greatly changes the image quality of the ultrasonic image has been adjusted, it is preferable to set a gain again in accordance with the adjusted image quality parameter. That is, it is preferable to activate the UI gated-gain update function. In this case, the user performs activating operation for the UI gated-gain update function via the UI. In contrast, when the user has adjusted an image quality parameter that does not much change the image quality of the ultrasonic image, it is not necessary to set a gain again in accordance with the adjusted image quality parameter. That is, it is preferable for the user not to perform activating operation for the UI gated-gain update function via the UI. In this case, the user does not perform activating operation for the UI gated-gain update function via the UI.

Upon determining in step SA12 that the user has performed activating operation (YES in step SA12), the system control unit 39 advances to step SA2. That is, upon receiving an input signal corresponding to the activating operation, the switching unit 275 activates the automatic STC adjusting function and the UI gated-gain update function of the automatic setting unit 273. The automatic setting unit 273 then executes the activated UI gated-gain update function and updates the gain based on the scanning conditions after adjustment. In this case, the system control unit 39 performs ultrasonic scanning under the scanning conditions newly adjusted in step SA10 with the gain set by the automatic setting unit 273 (UI gated-gain update function) based on the scanning conditions. That is, the gain set in step SA8 is reset.

Upon determining in step SA12 that the user has not performed activating operation (NO in step SA12), the system control unit 39 advances to step SA4. That is, the system control unit 39 performs ultrasonic scanning under the scanning conditions newly adjusted by the scanning condition setting unit 13 in step SA10 with the gain adjusted by the manual setting unit 271 in step SA8. In this case, the gain correction unit 29 corrects the echo signal with the gain adjusted by the manual setting unit 271.

When the system control unit 39 repeats ultrasonic scanning in this manner, and completes overall ultrasonic scanning, the user inputs an instruction to end ultrasonic examination via the UI. Upon receiving the instruction to end ultrasonic examination, the system control unit 39 ends ultrasonic scanning by controlling the respective units.

According to the above flowchart, the ultrasonic diagnosis apparatus 1 corrects an echo signal with the gain set in accordance with adjusting operation of the user via the UI or the gain automatically set in accordance with scanning conditions. More specifically, the ultrasonic diagnosis apparatus 1 automatically stops the UI gated-gain update function in response to the execution of STC adjusting operation as a trigger, and continues the UI gated-gain update function when STC adjusting operation is not performed. In addition, the ultrasonic diagnosis apparatus reactivates the UI gated-gain update function in response to activating operation for the UI gated-gain update function as a trigger after automatic stoppage of the UI gated-gain update function. In this manner, the ultrasonic diagnosis apparatus 1 can select between activating and stopping the UI gated-gain update function in accordance with an instruction from the user via the UI more flexibly than the prior art. With this function, when scanning conditions are adjusted after automatic stoppage of the UI gated-gain update function and the user does not want to perform automatic STC adjustment with the UI gated-gain update function under the scanning conditions, the ultrasonic diagnosis apparatus 1 can perform ultrasonic scanning under the adjusted scanning conditions with the gain having undergone STC adjustment via the UI. In other words, when scanning conditions are adjusted after automatic stoppage of the UI gated-gain update function, and the user does not want to perform automatic STC adjustment with the UI gated-gain update function in accordance with the scanning conditions, the user need not manually perform STC adjusting operation again via the UI. This improves the throughput of ultrasonic examination as compared with the prior art. Therefore, the ultrasonic diagnosis apparatus 1 according to the first embodiment achieves an improvement in efficiency in gain adjusting operation. In addition, this apparatus achieves an improvement in flexibility in gain selection, and hence also achieves an improvement in the quality of ultrasonic scanning.

As shown FIG. 1, the gain correction unit 29 is functionally provided between the envelope detection unit 25 and the image generating unit 31. However, this embodiment is not limited to this. It is possible to incorporate the gain correction unit 29 in any of constituent elements ranging from the reception unit 21 to the display unit 35. For example, the gain correction unit 29 may be incorporated in the logarithmic compression unit 23 to perform gain correction concurrently with logarithmic compression. Alternatively, the gain correction unit 29 may be incorporated in the reception unit 21 to perform gain correction concurrently with amplification of an echo signal from the input unit 11.

According to the above flowchart, when the overall brightness of an image is adjusted (2DGain adjusting operation is performed), the UI gated-gain update function is not stopped. However, this embodiment need not be limited to this. The switching unit 275 may stop the UI gated-gain update function in response to the execution of adjustment of the overall brightness of the image as a trigger.

Second Embodiment

An ultrasonic diagnosis apparatus according to the second embodiment automatically reactivates (reboots) the UI gated-gain update function in response to the execution of adjusting operation for a specific image quality parameter. The ultrasonic diagnosis apparatus having this function according to the second embodiment will be described below. The same reference numerals as in the first embodiment denote constituent elements having almost the same functions, and a repetitive description of such constituent element will be made only when necessary.

FIG. 4 is a block diagram showing the arrangement of an ultrasonic diagnosis apparatus 50 according to the second embodiment. As shown in FIG. 4, the ultrasonic diagnosis apparatus 50 includes, in a gain setting unit 27, a manual setting unit 271, an automatic setting unit 273, an item setting unit 277, and a switching unit 279.

The item setting unit 277 sets a specific item (image quality parameter) of scanning conditions for automatically reactivating the UI gated-gain update function in accordance with an instruction from the user via the UI of an input unit 11. This specific item will be referred to as a trigger parameter hereinafter. A trigger parameter is typically set to an item whose value is adjusted to result in a large change in the intensity of an echo signal and a large change in image quality. That is, a trigger parameter is an item that requires automatic adjustment of a gain by the UI gated-gain update function. One or a plurality of trigger parameters may be used.

It is possible to set any of the above image quality parameters as a trigger parameter. For example, it is preferable to set a scanning mode, transmission/reception frequency, or focus position as a trigger parameter.

The switching unit 279 reactivates the UI gated-gain update function of the automatic setting unit 273 which is inactive, in response to the execution of trigger parameter adjusting operation by the user via the input unit 11 as a trigger.

When a gain is set by the manual setting unit 271 and the image quality parameter adjusted by the scanning condition setting unit 13 is a trigger parameter, a gain correction unit 29 according to the second embodiment corrects the echo signal with the gain set by the automatic setting unit 273 based on the adjusted image quality parameter. When the manual setting unit 271 has set a gain and the image quality parameter adjusted by the scanning condition setting unit 13 is not a trigger parameter, the gain correction unit 29 according to the second embodiment corrects the echo signal with the gain set by the manual setting unit 271.

Figure 5:
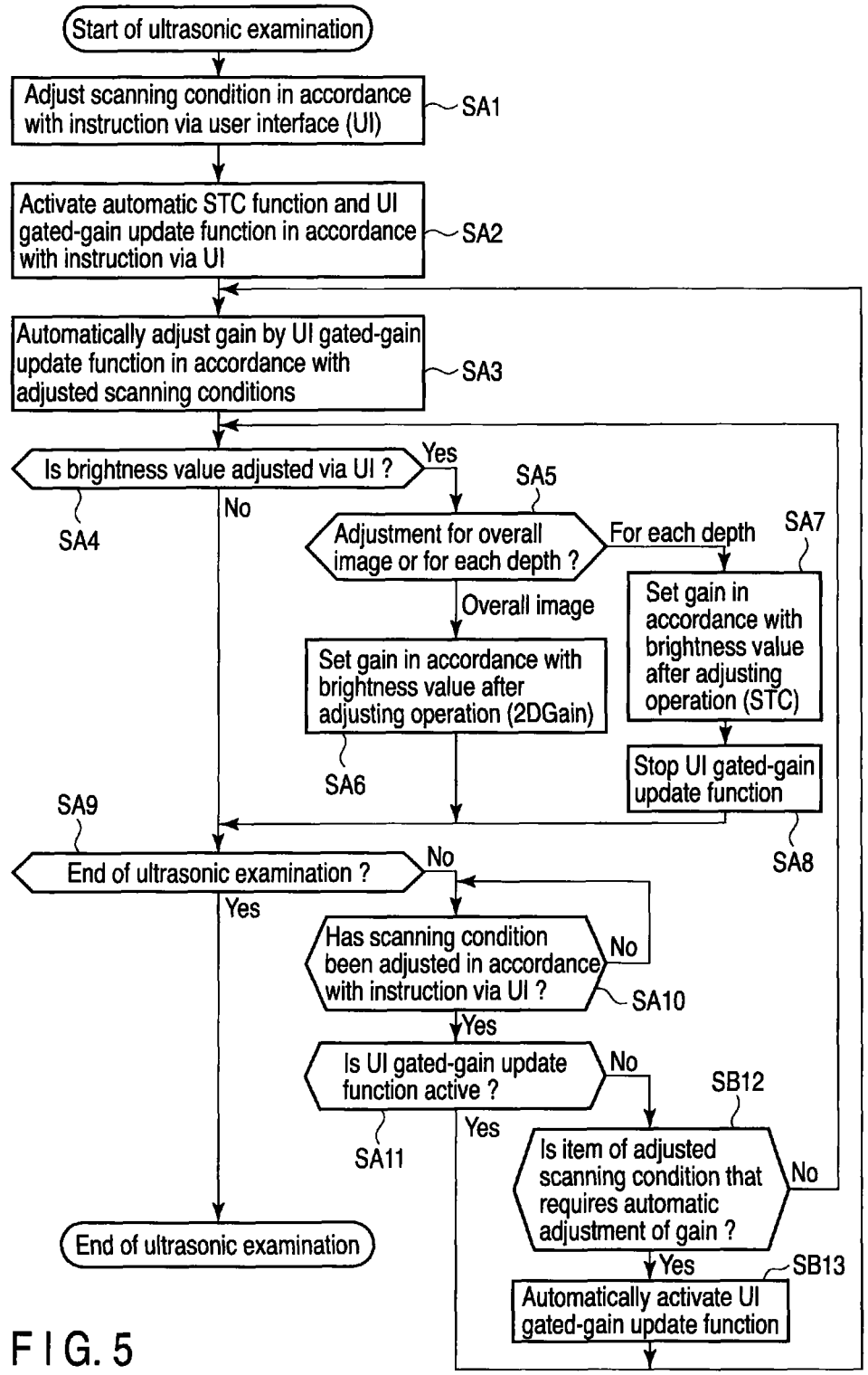
FIG. 5 is a flowchart showing a typical example of a procedure in ultrasonic examination performed under the control of a system control unit in FIG. 4.

A flowchart for ultrasonic examination performed by using a gain setting method unique to the second embodiment will be described next. FIG. 5 is a flowchart showing a typical example of a procedure in ultrasonic examination performed under the control of the system control unit 39 in the second embodiment. Assume that before the following flowchart is executed, the item setting unit 277 has set a trigger parameter. Assume also that the code of the set trigger parameter is stored in the memory in the item setting unit 277. In the following description of the flowchart, the same step numbers as in the flowchart in the first embodiment denote the same processes, and a description of them will be omitted.

When the processing proceeds in the following sequence: (YES in step SA4)→(step SA5: for each depth)→(step SA7)→(step SA8)→(NO in step SA9)→(YES in step SA10), the UI gated-gain update function of the automatic setting unit 273 is not active at the time of step SA11. Upon determining in step SA11 that the UI gated-gain update function is not active (NO in step SA11), a system control unit 39 advances to step SB12.

Upon determining in step SA11 that the UI gated-gain update function is not active (NO in step SA11), the system control unit 39 causes the switching unit 279 to perform trigger parameter determination processing (step SB12). In step SB12, the switching unit 279 determines whether the image quality parameter adjusted in step SA10 is a parameter that requires automatic adjustment of a gain. More specifically, the switching unit 279 determines whether the code of the image quality parameter adjusted in step SA10 coincides with the code of the trigger parameter set by the item setting unit 277.

Upon determining that the image quality parameter adjusted in step SA10 does not coincide with the code of the trigger parameter, the switching unit 279 determines that the image quality parameter adjusted in step SA10 is not a parameter that requires automatic adjustment of a gain, i.e., a trigger parameter (NO in step SB12). In this case, the image quality parameter adjusted in step SA10 is typically an image quality parameter that does not greatly change the image quality. That is, it is not necessary to set a gain again in accordance with the adjusted image quality parameter, and it is preferable not to activate the UI gated-gain update function. In this case, the system control unit 39 advances to step SA4. The system control unit 39 then performs ultrasonic scanning under the scanning conditions newly adjusted by the scanning condition setting unit 13 in step SA10 with the gain adjusted by the manual setting unit 271 in step SA8.

Upon determining in step SA10 that the adjusted image quality parameter coincides with the code of the trigger parameter, the switching unit 279 determines that the image quality parameter adjusted in step SA10 is a parameter that requires automatic adjustment of the gain, i.e., a trigger parameter (YES in step SB12). In this case, the system control unit 39 causes the switching unit 279 to reactivate the UI gated-gain update function (step SB13). When the UI gated-gain update function is reactivated, the system control unit 39 advances to step SA3. That is, the automatic setting unit 273 executes the UI gated-gain update function, and updates the gain based on the scanning conditions newly adjusted in step SA10. That is, the system control unit 39 performs ultrasonic scanning under the scanning conditions newly adjusted by the scanning condition setting unit 13 in step SA10 with the gain adjusted by the automatic setting unit 273 based on the scanning conditions.

When ultrasonic scanning is repeated in this manner, and ultrasonic scanning is complete, the user inputs an instruction to end ultrasonic examination via the UI. Upon receiving the instruction to end ultrasonic examination, the system control unit 39 ends ultrasonic scanning by controlling the respective units.

According to the above flowchart, the ultrasonic diagnosis apparatus 50 automatically reactivates the UI gated-gain update function in response to the execution of adjusting operation for a specific image quality parameter (trigger parameter) set in advance by the user as a trigger. This makes it unnecessary for the user to manually reactivate the UI gated-gain update function. This therefore improves the throughput of ultrasonic examination. The ultrasonic diagnosis apparatus 50 according to the second embodiment achieves an improvement in efficiency in gain adjusting operation.

Each function associated with each embodiment can also be implemented by installing programs for executing the corresponding processing in a computer such as a workstation and mapping them in a memory. In this case, the programs which can cause the computer to execute the corresponding techniques can be distributed by being stored in recording media such as magnetic disks (Floppy® disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnosis apparatus, comprising:
   an ultrasonic probe;
   a transmitter configured to transmit an ultrasonic wave to a subject through the ultrasonic probe;
   a receiver configured to receive an ultrasonic wave reflected by the subject through the ultrasonic probe and generate an echo signal corresponding to the received ultrasonic wave;
   a processing circuit configured to
      control the transmitter and the receiver to repeat ultrasonic scanning through the ultrasonic probe, and
      adjust a scanning condition for the repeated ultrasonic scanning in accordance with an instruction from a user;
   a setting circuit including an automatic gain setting circuit configured to have a first automatic function and a second automatic function, and to have a manual setting circuit configured to set the gain in accordance with an instruction given from the user, the first automatic function automatically setting the gain for correcting the echo signal in accordance with the adjusted scanning condition, the second automatic function automatically setting the gain based on the echo signal,
   wherein the processing circuit is further configured to
      correct the echo signal with the gain set by the manual setting circuit in accordance with the instruction from the user, when the processing circuit adjusts the scanning condition and the first automatic function is inactive, and correct the echo signal with the gain set by the second automatic function, when the processing circuit adjusts the scanning condition and the first automatic function is active; and
      generate ultrasonic image data based on the corrected echo signal.

2. The ultrasonic diagnosis apparatus according to claim 1, wherein the processing circuit inactivates the first automatic function, when the manual setting circuit sets the gain and the processing circuit adjusts a specific item of a plurality of items associated with the scanning condition.

3. The ultrasonic diagnosis apparatus according to claim 2, wherein the processing circuit is further configured to set the specific item in accordance with an instruction from the user.

* * * * *